United States Patent
Aardsma

(10) Patent No.: US 11,458,150 B2
(45) Date of Patent: Oct. 4, 2022

(54) METHYLPHOSPHINIC ACID COMPOSITIONS AND METHODS FOR REDUCING AGING

(71) Applicant: Gerald E. Aardsma, Loda, IL (US)

(72) Inventor: Gerald E. Aardsma, Loda, IL (US)

(73) Assignee: Gerald E. Aardsma, Loda, IL (US)

( * ) Notice: Subject to any disclaimer, the term of this patent is extended or adjusted under 35 U.S.C. 154(b) by 252 days.

(21) Appl. No.: 16/936,168

(22) Filed: Jul. 22, 2020

(65) Prior Publication Data

US 2021/0023097 A1     Jan. 28, 2021

Related U.S. Application Data

(60) Provisional application No. 62/877,729, filed on Jul. 23, 2019.

(51) Int. Cl.
| | | |
|---|---|---|
| *A61K 31/662* | (2006.01) | |
| *A61P 43/00* | (2006.01) | |
| *A23L 29/00* | (2016.01) | |
| *A23L 33/10* | (2016.01) | |

(52) U.S. Cl.
CPC ............ *A61K 31/662* (2013.01); *A23L 29/05* (2016.08); *A23L 33/10* (2016.08); *A61P 43/00* (2018.01)

(58) Field of Classification Search
None
See application file for complete search history.

(56) References Cited

U.S. PATENT DOCUMENTS

| | | | |
|---|---|---|---|
| 4,016,264 A | | 4/1977 | Clark |
| 4,637,885 A | * | 1/1987 | Kuwamoto .......... C10M 137/08 508/436 |
| 2019/0000125 A1 | | 1/2019 | Aardsma |

OTHER PUBLICATIONS

Aardsma, Aging Cause & Cure. ARP Aardsma Research & Publishing. 148 pages, (2017).
Aardsma, Aging: Cause and Cure, Part IL 14 pages, Jul. 9, 2019.
Aardsma, Human Aging is a Two-Phase Disease. The Biblical Chronologist. May 13, 2020;10(8):1-10.
Aardsma, Intake Recommendations for Dr. Aardsma's Anti-Aging Vitamins. The Biblical Chronologist. Jun. 10, 2020 ; 10(10): 1-8.
Boah, Preventing Animal Warts, Indiana State Board of Animal Health-Tech Bulletin RC4-11.98. Retrieved online at https://www.in.gov/boah/files/Animal%20Wart%20Prevention%2011-12.pdf. 2 pages, (2011).

* cited by examiner

*Primary Examiner* — Jeffrey S Lundgren
*Assistant Examiner* — Michael J Schmitt
(74) *Attorney, Agent, or Firm* — McCarter & English, LLP; Jonathan M. Sparks; Michael J. DeGrazia

(57) ABSTRACT

A composition that includes methylphosphinic acid or a salt thereof, and optionally methylphosphonic acid or a salt thereof, and an ingredient acceptable for consumption by a mammal is provided herein. Also provided is a method for reducing aging in a mammal that involves providing or administering methylphosphinic acid or a salt thereof, and optionally, methylphosphonic acid or a salt thereof, to the mammal in need thereof for consumption. A composition for use in such a method and an article useful for such a method include those in the form of a food product such as a prepackaged or processed food or meal, a beverage, a nutritional supplement, or a nutraceutical.

16 Claims, 5 Drawing Sheets

METHYLPHOSPHINIC ACID COMPOSITIONS AND METHODS FOR REDUCING AGING

CROSS REFERENCE TO RELATED APPLICATIONS

This application claims priority to U.S. Provisional Patent Application No. 62/877,729, filed on Jul. 23, 2019, the content of which is incorporated herein by reference in its entirety.

BACKGROUND

It has been reported that aging leading to physical decline occurs in humans as early as the third decade of life. Besdine, R. W., Changes in the Body with Aging, MERCK MANUALS, Merck Sharp & Dohme Corp, 2018, available at www.merckmanuals.com/home/older-people %E2%80%99s-health-issues/the-aging-body/changes-in-the-body-with-aging (last visited Jun. 20, 2018).

Aging leads to a gradual and continuous decline that involves loss of function at the cellular level, as well as the level of the organs and body systems. Aging affects not only the bones and muscles, but also the joints, body fat, the eyes, the ears, the mouth and nose, the skin, the brain and nervous system, the heart and blood vessels, the muscles involved in breathing, the lungs, the digestive system, the kidney and urinary tract, the reproductive system, the endocrine system, blood, and the immune system. See Besdine.

Thus, the ability to reduce aging or increase life span provides many benefits.

SUMMARY

The invention relates to aging, in particular, to reducing aging in a mammal. The invention is based on the discovery that methylphosphinic acid (MePiA) and optionally, methylphosphonic acid (MePA), in the diet can reduce aging in a mammal. Thus, the present disclosure provides a composition and a method for reducing aging and/or improving health. The present disclosure provides a composition for consumption by a mammal that includes MePiA or a salt thereof, optionally, MePA or a salt thereof, and an ingredient acceptable for consumption by a mammal. The present disclosure also provides a method of use that involves providing or administering a composition that has MePiA or a salt thereof, or both MePiA or a salt thereof and MePA or a salt thereof, and an ingredient acceptable for consumption by a mammal, as well as a method of use that involves providing or administering MePiA or a salt thereof, MePA or a salt thereof, or both MePiA or a salt thereof and MePA or a salt thereof.

In one aspect, the present disclosure provides a composition that includes methylphosphinic acid or a salt thereof and an ingredient acceptable for consumption by a mammal. In some embodiments, the ingredient acceptable for consumption by a mammal is an ingredient generally regarded as safe for human consumption.

In some embodiments, the composition is a liquid in which the methylphosphinic acid or a salt thereof is at a concentration of about 2 mg/L to about 600 mg/L. In some embodiments, the composition is a beverage in which the methylphosphinic acid or a salt thereof is at a concentration of about 0.005 mg/L to about 1 mg/L. In some embodiments, the composition further includes methylphosphonic acid or a salt thereof. In some embodiments, the composition includes about equal amounts of (a) the methylphosphinic acid or a salt thereof, and (b) the methylphosphonic acid or a salt thereof.

In some embodiments, the composition is a solid or semi-solid that has about 0.3 mg to about 2 g of the methylphosphinic acid or a salt thereof per kilogram of the solid. In some embodiments, the composition is prepackage food that has about 0.01 mg to about 5 mg of the methylphosphinic acid or a salt thereof per kilogram of the prepackaged food. In some embodiments, the solid or semi-solid composition further includes methylphosphonic acid or a salt thereof. In some embodiments, the composition has about equal amounts of (a) the methylphosphinic acid or a salt thereof, and (b) the methylphosphonic acid or a salt thereof. In some embodiments, the composition is a powder that has about 1 mg/kg to about 2 g/kg of the methylphosphinic acid or a salt thereof.

In another aspect, the present disclosure provides a composition consisting essentially of methylphosphinic acid or a salt thereof and one or more ingredients acceptable for consumption by a mammal. In some embodiments, the ingredient acceptable for consumption by a mammal is an ingredient generally regarded as safe for human consumption. In some embodiments, the composition further includes methylphosphonic acid or a salt thereof. In some embodiments, the composition is a liquid consisting essentially of about 0.005 mg/L to about 600 mg/L of the methylphosphinic acid or a salt thereof. In some embodiments, the composition is a solid consisting essentially of about 0.01 mg/kg to about 2 g/kg of the methylphosphinic acid or a salt thereof.

In another aspect, the present disclosure provides a method for reducing aging in a mammal, the method involves providing or administering to the mammal a composition disclosed herein that includes methylphosphinic acid or a salt thereof and an ingredient acceptable for consumption by a mammal. In some embodiments, the method involves providing or administering to the mammal a composition disclosed herein that includes methylphosphinic acid or a salt thereof and an ingredient generally regarded as safe for human consumption.

In another aspect, the invention provides a consumable article comprising a composition of the invention, sealed packaging material within which the composition is disposed, and printed text comprising information pertaining to the composition, wherein the printed text is on the surface of the packaging material, on a label affixed to the packaging material, or provided as an accompanying insert of the article.

In one embodiment, the article is a beverage, wherein the sealed packaging material is a container effective to hold a liquid without leaking and within which the composition is disposed, wherein the composition is a beverage comprising methylphosphinic acid or a salt thereof, and optionally methylphosphonic acid or a salt thereof.

In one embodiment, the article is prepackaged food.

In another aspect, the invention provides a composition for human consumption consisting essentially of methylphosphinic acid or a salt thereof, and optionally methylphosphonic acid or a salt thereof, and one or more ingredients acceptable for human consumption.

As used herein, the singular forms "a", "an", and "the" include plural reference unless the content clearly dictates otherwise.

As used herein, the term "about" in reference to a numeric value means within 10% of the specified value, i.e., within + or −10% of a reference value.

Any feature or combination of features described herein are included within the scope of embodiments of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION

Figure 1:
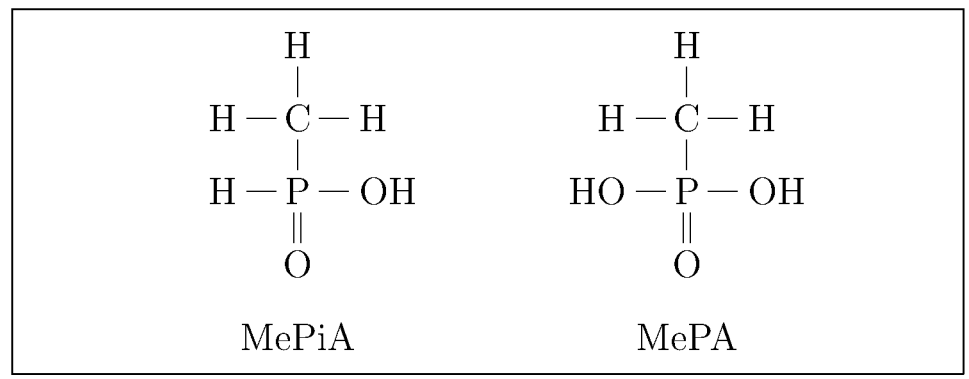
FIG. 1 illustrates the chemical structure of methylphosphinic acid (MePiA) and methylphosphonic acid (MePA).

The invention relates to aging, in particular, to reducing aging in a mammal. The invention is based on the discovery that methylphosphinic acid (MePiA) and optionally, methylphosphonic acid (MePA), can be used as a vitamin in the diet to reduce aging in a mammal. Thus, the present disclosure provides a composition and a method for reducing aging and/or improving health. The present disclosure provides a composition for consumption by a mammal that includes MePiA or a salt thereof, optionally, MePA or a salt thereof, and an ingredient acceptable for consumption by a mammal. The present disclosure also provides a method of use that involves providing or administering a composition that has MePiA or a salt thereof, or both MePiA or a salt thereof and MePA or a salt thereof, and an ingredient acceptable for consumption by a mammal, as well as a method of use that involves providing or administering MePiA or a salt thereof, MePA or a salt thereof, or both MePiA or a salt thereof and MePA or a salt thereof.

Methylphosphinic Acid

Methylphosphinic acid (MePiA) refers to a compound of linear formula $CH_3P(O)(OH)H$. As used herein, the term "methylphosphinic acid" or "MePiA" also includes methylphosphinate. The invention provides for the use of MePiA, as well as salts thereof. Examples of salts of MePiA include alkali metal or alkaline earth metal salts such as sodium, potassium, lithium, calcium, or magnesium salts thereof. Salts of MePiA may be obtained using standard procedures well known in the art.

Compositions of MePiA

The invention provides compositions containing MePiA or a salt thereof formulated for consumption by a mammal. The term "formulated for consumption by a mammal" means formulated with one or more ingredients acceptable for ingestion by the mammal. The term "consume" or "consumption" means to "ingest" or "ingestion," respectively. The term "mammal" is well understood in the art and includes a mouse, a pig, a cow, a horse and a human. A composition formulated for consumption can be one formulated as a food, a drink, or a dietary or nutritional supplement for mammalian use.

A composition formulated for consumption by a mammal is one that is substantially free of a substance that is unsafe or toxic for use in mammalian food, drink, or a dietary or nutritional supplement. Substances that are unsafe or toxic for mammalian consumption are known in the art. These include ingredients not generally recognized as safe or not approved for use in human food, beverage, or dietary supplement as known in the art. See, for example, 21 C.F.R. §§ 189. A substance that is unsafe or toxic also includes a substance that is present at a level that is not approved for human use in food, drink, or dietary supplement.

A composition formulated for consumption by a mammal includes MePiA or a salt thereof and at least one ingredient acceptable for consumption by the mammal. Ingredients acceptable for consumption by a mammal include those that are approved by the Food and Drug Administration for use in human food, beverage, or dietary supplement. Ingredients acceptable for human consumption are generally regarded as safe (GRAS). Ingredients that have GRAS status are well known in the art and can be found in the FDA's GRAS Notice Inventor. This is accessible at www.accessdata.fda-.gov/scripts/fdcc/?set=-GASNotices.

Thus, a composition formulated for consumption by a mammal can include one or more ingredients that are used in human food, beverages and dietary supplement. See, for example, the FDA database Everything Added to Food in the United States (EAFUS), which is accessible at www.accessdata.fda.gov/scripts/fcn/fcnNavigation.cfm?rpt=eafusListing. See also the database Substances Added to Food Inventory, which is provided by the FDA and accessible at www.accessdata.fda.gov/scripts/fdcc/?set=FoodSubstances. See also The Codex General Standardfor Food Additives (GSFA, Codex STAN 192-1995), Adopted in 1995 with latest revision in 2016, CODEX ALIMENTARIUS, INTERNATIONAL FOOD STANDARDS, which is accessible at www.fao.org/gsfaonline/index.html?print=true. Further, see, for example, Dietary Supplement Label Database provided by the National Institutes of Health, Office of Dietary Supplements, which is available at the website https//ods.od.nih.gov/Research/Dietary_Supplement_Label_Database.aspx; see also Dietary Supplement Products & Ingredients, available at www.fda.gov/Food/DietarySupplements/ProductsIngredients/. See also *Premarket Notification for a New Dietary Ingredient*, Federal Register, Volume 62, No. 184.

A composition formulated for consumption by a mammal can be a food product, a drink or beverage, or a dietary supplement for human use. A composition formulated for consumption by a mammal can be a liquid, a powder, or a solid formulated with one or more ingredients, for example and without limitation, a carrier, one or more food additives, one or more vitamins, one or more dietary supplement, or one or more other food or beverage ingredients. Thus, the composition can be formulated as a vitamin, part of a multi-vitamin, a beverage, a health drink, a nutritional bar, a condiment or any other pre-packaged food or beverage in liquid, solid, or semi-solid form. The composition can be a freeze-dried, condensed, frozen or pasteurized food, beverage, nutritional supplement or nutraceutical to which a select amount of MePiA or a salt thereof has been added.

A composition formulated for consumption by a mammal can be a hard or soft shell gelatin capsule, compressed into a tablet, or incorporated directly with food in the subject's diet. MePiA or a salt thereof can be combined with one or more excipients and used in the form of ingestible tablets, troches, capsules, elixirs, suspensions, syrups, wafers, and the like.

Tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. When the unit dosage form is a capsule, it can contain a liquid carrier, such as a vegetable oil or a polyethylene glycol. Various other materials such as coatings can be used to otherwise modify the physical form of the solid unit dosage form. Tablets, pills, or capsules, for example, can be coated with gelatin, wax, shellac or sugar and the like. A syrup or elixir can contain MePiA or a salt thereof, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed.

A composition formulated for consumption by a mammal can be a sterile injectable solution prepared by incorporating MePiA or a salt thereof in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Ingredients acceptable for consumption by a mammal include, in addition to MePiA or a salt thereof, one or more of the following without limitation: a carbohydrate such as one or more sugars; vitamin A (e.g. retinyl palmitate); vitamin C (e.g. ascorbic acid and sodium ascorbate); vitamin D (e.g. cholecalciferol); vitamin E (e.g. dl-alpha-tocopheryl acetate); vitamin B-6 (e.g. pyridoxine HCl); folic acid; vitamin B-12 (cyanocobalamin); biotin; pantothenic acid (calcium d-pantothenate); iodine (e.g. potassium iodine); zinc (e.g. zinc chelate); choline (e.g. choline bitartrate); inositol; calcium (e.g. tricalcium phosphate); phosphorus (e.g. tricalcium phosphate); sodium; sucrose; glucose syrup; gelatin; canola lecithin; citric acid; a food coloring agent including annatto extract, blueberry and carrot concentrates, and purple carrot juice; lactic acid; medium chain triglycerides; natural flavors and pectin; high fructose corn syrup; corn syrup; boysenberry juice; citric acid; xantham gum; cellulose gum; caramel color; salt; sodium benzoate and sorbic acid; sodium hexametaphosphate; iron; fiber and any combination thereof.

A composition comprising MePiA or a salt thereof can be a liquid or a solid form. A composition comprising MePiA or a salt thereof can also include MePA, in which case the MePiA and MePA can be present at similar amounts.

A composition comprising MePiA or a salt thereof can be provided in a concentrated liquid form, for example, at a concentration between about 2 mg/L to about 600 mg/L. As such, the liquid form can be used as an additive to a food, drink or beverage. Thus, MePiA or a salt thereof can be provided as a liquid having a concentration of, for example and without limitation, about 2 mg/L, about 4 mg/L, about 10 mg/L, about 20 mg/L, about 50 mg/L, about 100 mg/L, about 150 mg/L, about 200 mg/L, about 250 mg/L, about 300 mg/L, about 350 mg/L, about 400 mg/L, about 450 mg/L, about 500 mg/L, about 550 mg/L or more than about 550 mg/L of MePiA or a salt thereof where the composition also includes MePA, the MePA can be present in a concentration similar to that of MePiA.

Alternatively, the MePiA or a salt thereof can be included in a drink, beverage or liquefied food such as a can of soup at a concentration between about 0.005 mg to about 1 mg of the MePiA per liter (L) of the beverage or liquefied food. In these embodiments, the MePiA or a salt thereof can be present at, for example and without limitation, about 0.005 mg/L, about 0.01 mg/L, about 0.02 mg/L, about 0.03 mg/L, about 0.04 mg/L, about 0.05 mg/L, about 0.6 mg/L, about 0.7 mg/L, about 0.08 mg/L, about 0.09 mg/L, about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, or more than about 0.9 mg/L. Where the composition also includes MePA, the MePA can be present in a concentration similar to that of MePiA.

MePiA or a salt thereof can be formulated as a solid or powder having about 0.3 mg to about 2 grams of MePiA or a salt thereof per kilogram of the solid or powder. As such, the solid or powder containing the MePiA or a salt thereof can be used as food or beverage additive. In these embodiments the solid or powder can have, for example and without limitation, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, or more than about 1.9 mg of MePiA or salt thereof per kilogram of the solid or powder. Where the composition also includes MePA, the MePA can be present in an amount similar to that of MePiA.

Alternatively, MePiA or a salt thereof can be included as part of a processed or prepackaged food at a concentration of about 0.01 mg to about 5 mg of MePiA per kilogram of the processed or prepackaged food. As such the processed or prepackaged food can be prepared with, for example and without limitation, about 0.01 mg/kg, about 0.02 mg/kg, about 0.05 mg/kg, about 0.1 mg/kg, about 0.15 mg/kg, about 0.2 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, or more than about 4.5 mg/kg of MePiA or a salt thereof. Where the composition also includes MePA, the MePA can be present in an amount similar to that of MePiA.

Methods of Using MePiA or Compositions of MePiA

The present disclosure provides a method for reducing aging in a mammal that involves administering MePiA or a salt thereof to the mammal.

The term "aging" refers to a loss, decline or deterioration of any one or more body functions or appearance resulting in increasing debilitation and elderliness. Aging includes a deterioration in any one or more conditions of the body, as well as a development of one or more diseases or medical conditions and any associated effects or clinical symptoms that typically occur as a mammal, such as a human, advances in age. Aging includes loss, decline or deterioration of one or more body functions that can take place at the cellular level, as well as the level of one or more organs or body systems and can be observed as a decline in physical, mental or psychological health including an individual's fitness, appearance or wellbeing. The loss, decline or deterioration of one or more body functions can increase the propensity for physical injury, increase susceptibility to a disease such as an infectious disease, or accelerate development of a disease or medical condition to which an individual is predisposed.

As used herein, the term "reducing aging" means lessening, decreasing, or alleviating aging, the appearance of aging including loose or sagging skin, the number of symptoms associated with aging, or the loss or deterioration associated with aging, as well as the severity of the symptoms associated with aging. The term "reducing aging" also includes delaying the onset of aging or its associated health decline, as well as prolonging or extending life span by any observable degree. Aging is reduced if one or more of the foregoing symptoms, loss, or deterioration is lessened, decreased, or alleviated by any observable amount.

The present disclosure provides a method for reducing aging in a mammal that involves providing or administering to the mammal in need thereof MePiA or a salt thereof, and optionally MePA or a salt thereof. The present disclosure also provides a method for reducing aging that involves providing or administering to a mammal in need thereof a composition that contains MePiA or a salt thereof, optionally, MePA or a salt thereof, and an ingredient acceptable for human consumption. The composition can be, without limitation, a beverage, a pre-processed or pre-packaged food item such as a nutritional bar, a prepared meal, or a dietary supplement in the form of a vitamin or multivitamin. The methods provided herein can include identifying an individual in need of increasing life span or reducing aging or its associated physical or mental deterioration, and administering to the individual MePiA, a salt thereof, or a composition comprising MePiA or a salt thereof, optionally with MePA or a salt thereof. An individual in need of increasing life span or reducing aging and/or its associated physical or mental deterioration can be identified based on age, based on a loss, decline or deterioration of one or more body function or appearance, as well as their associated effects or symptoms including, without limitation: (1) development of one or more diseases or medical conditions; (2) an increase in the propensity for physical injury; (3) an increase in susceptibility to a disease; (4) an acceleration or worsening of a disease or medical condition to which an individual is predisposed; (5) a decline in physical, mental or psychological fitness or wellbeing; and (6) a deterioration in appearance including loss of skin health, firmness and/or youthful appearance.

Articles of the Invention

The invention also provides articles in the form of packaging within which MePiA, a salt thereof, and optionally, MePA or a salt thereof, are disposed that can be conveniently provided to a mammal including a human. The article can be, for example and without limitation, (1) a sealed pouch containing a single serving of MePiA or a salt thereof in solid, powder or chewable form, or a composition that includes MePiA or a salt thereof in which the MePiA or a salt thereof is between about 0.01 mg/kg to about 5 mg/kg; (2) a bottle containing MePiA or a salt thereof between about 0.01 mg/kg to about 5 mg/kg in solid, powder or chewable form; (3) a beverage contained within a leak-proof container such as a glass bottle, a can or a box container known in the art for holding a fluid in which the MePiA or a salt thereof is present about 0.005 mg/L to about 1 mg/L; (4) a pre-packaged food product in which a food or meal fortified with about 0.01 mg/kg to about 5 mg/kg of MePiA or a salt thereof is contained in a microwaveable or oven-proof sealed tray; or (5) a can food item in which the food or meal contained within is fortified with 0.005 mg/L to about 1 mg/L of MePiA or a salt thereof.

In the forgoing embodiments, the article can be a pre-packaged item such as: (1) an infant formula or baby food in solid, semi-solid or liquid form; (2) milk or other beverage in a carton, bottle or single serving box; (3) a pre-cooked or uncooked meal; and (4) an edible item that is frozen, freeze-dried or otherwise preserved and packaged.

In addition to the MePiA or a salt thereof, the forgoing embodiments can also include MePA or a salt thereof in any amount including, for example, in an amount less than or equal to the amount of MePiA or a salt thereof.

Articles of the invention include printed text pertaining to the contents of the article. Printed text can be on the packaging material, e.g. printed on an exterior surface of the packaging material, on a label affixed to the packaging material, or on an accompanying label insert. The printed text can include any information pertaining to MePiA or a salt thereof that may be useful to the individual in need thereof including, without limitation, the ingredient(s) contained within, quantities thereof, and/or directions of use thereof.

The foregoing description and following examples are intended to illustrate and not limit the scope of the invention defined by the scope of the claims.

EXAMPLES

Example 1: Methylphosphonic Acid (MePA) and Salts and Compositions Thereof

MePA [CAS Number 993-13-5; Linear Formula $CH_3P(O)(OH)_2$; Molecular Weight 96.02] is commercially available. MePA was obtained from MilliporeSigma (formerly Sigma-Aldrich) (product number 289868). A dietary supplement of 2 micrograms of MePA per day was prepared as follows. A solution containing 0.0040 grams of MePA in 100 milliliters of distilled water was prepared in a dropper bottle. This solution contained 2 micrograms of MePA per 50 microliters of water. Fifty microliters is the approximate volume of a drop of water. A drop of said solution was dispensed from said dropper bottle into a drinking cup and the cup was filled with drinking water to produce a once per day dietary supplement of MePA of about 2 micrograms.

Example 2: Safety of MePA Supplementation

There is no known risk to health, from either theory or experiment, due to inclusion of MePA in the diet in microgram per day amounts. Low toxicity is normal for the water-soluble vitamins. Safety of MePA is theoretically assured by the smallness of the daily dose and the water solubility of MePA. Toxicity studies in human volunteers and in animals have revealed no signs of any toxicity, even at very large doses.

MePA highly dissociates at physiological pH based on its pKa values ($pKa_1=2.12$ and $pKa_2=7.29$) and does not bio-accumulate. Because MePA is water soluble, excess MePA is rapidly eliminated from the body by the kidneys.

The low dosage of MePA combined with MePA's rapid elimination from the body in the urine makes expectation of toxicity unreasonable. The effect of the smallness of the dose is illustrated by comparison to the deadly synthetic compound sarin, which is used as a chemical weapon due to its extreme potency as a toxic nerve agent. A single dose of 500 micrograms (at least a factor of 10 above a reasonable daily vitamin MePA supplementation dose rate) administered to a healthy male volunteer, caused only "mild symptoms of intoxication." [https://en.wikipedia.org/wiki/Sarin.]

Seven months of supplementation of the diets of 36 ICR (Harlan) female mice at 100 mg MePA/liter in their drinking water beginning at 5.7 months of age yielded no symptoms of toxicity. This is equivalent to human MePA supplementation at roughly 250,000 micrograms of MePA per day.

Eight months of supplementation of the diets of two mature female cats at 2 micrograms MePA/day yielded no symptoms of toxicity. This is equivalent to human MePA supplementation at roughly 30 micrograms per day.

Eight months of supplementation of the diets of two mature male dogs at 10 micrograms MePA/day yielded no symptoms of toxicity. This is equivalent to human MePA supplementation at roughly 50 micrograms per day.

Human tests of MePA supplementation with 10 volunteers lasting at least five months for all volunteers and as long as thirty-one months for one volunteer, with doses in the range of 1 to 50 micrograms per day, yielded no symptoms of toxicity.

Example 3: Daily MePA Dietary Supplementation & Associated Health Benefits

MePA was administered as a dietary supplement to 10 pilot study volunteers. Testing was conducted in three phases: phase 1 involved a single volunteer participant; phase 2 included one additional volunteer, giving two participants total; and phase 3 included an additional eight volunteers, giving a total of ten participants. MePA doses varied, typically between 1 and 6 micrograms of MePA per day.

To objectify sleep experiences, which, early on, were observed to benefit from vitamin MePA supplementation, several participants were equipped with commercially available Fitbit Charge 2 bracelets. These devices automatically recorded activity and heart rate data, from which sleep stages were estimated by a Fitbit app on a daily basis. No negative side effects due to MePA supplementation were reported by any of the volunteers. Significant health benefits were reported in most instances. Recurrent observations across multiple volunteers, implying therapeutic action due to the MePA vitamin, included improved sleep, reduced pain, diminished headaches/migraines, more rapid healing, improved immune function, improved mental health, more youthful skin, increased energy, improved heart function, and decreased nocturia.

Participant A was a 60-year-old male diagnosed in his early 50's with chronic inflammatory demyelinating polyneuropathy (CIDP), an autoimmune disease in which the immune system attacks the myelin sheath surrounding nerves resulting in loss of nerve impulses to peripheral muscles, with ensuing weakness. At the time of diagnosis, Participant A had difficulty lifting his fork to feed himself, was unable to button his shirt or move a blanket, and was unable to walk up or down stairs unassisted. The symptoms of CIDP experienced by Participant A improved substantially though not completely with several standard treatment regimens including high prednisone, then IV-Ig, and finally 60 ml Hizentra home infusions twice per week.

Participant A received a daily supplement of MePA according the following dose history: (a) 1 microgram/day beginning 2015 Nov. 26; (b) 0 micrograms/day beginning 2016 Feb. 25; (c) 1 microgram/day beginning 2016 Feb. 28; (d) 0 micrograms/day beginning 2016 Mar. 5; (e) 1 microgram/day beginning 2016 May 14; (f) 0 micrograms/day beginning 2016 May 26; (g) 1 microgram/day beginning 2016 Jul. 18; (h) 0 micrograms/day beginning 2016 Aug. 15; (i) 1 microgram/day beginning 2016 Sep. 15; (j) 2 micrograms/day beginning 2017 Jun. 9; (k) 4 micrograms/day beginning 2017 Jul. 16; (l) 50 micrograms/day beginning 2017 Aug. 12; (m) 0 micrograms/day beginning 2017 Aug. 25; (o) 6 micrograms/day beginning 2017 Aug. 26; (p) 4 micrograms/day beginning 2017 Dec. 30; (q) 8 micrograms/day beginning 2018 Feb. 3; and (r) 6 micrograms/day beginning 2018 Mar. 12. Participant A experienced no adverse side effects from MePA supplementation.

With MePA supplementation at 1 microgram/day, Participant A reported positive health effects at three and a half weeks. Participant A reported an improvement in leg muscle strength and stamina. Prior to treatment, the participant was able to walk one mile a day; this distance increased to two miles a day after three and a half weeks of MePA supplementation. After five and a half weeks of treatment, Participant A could forgo the biweekly infusions for CIDP without noticeable loss of muscle strength or stamina. The positive health effects and improvement of CIDP had not diminished as of the final report, nearly two and a half years after MePA supplementation began. Additional health benefits associated with MePA supplementation reported by Participant A included improved sleep, less frequent headaches and migraines, more rapid healing, enhanced immune function, more youthful skin, decreased sensitivity to cold, improved circulation and increased psychological energy. The following specific health benefits were reported by Participant A:

Improved sleep as evidenced by sleep being deeper and less interrupted, resulting in less sleep needed and feeling more rested;

Less frequent headaches and migraines, declining rapidly from a once-every-two-weeks occurrence frequency to almost no occurrence of headaches or migraines for several months;

More rapid healing as evidenced by a quick cessation of muscle pain in the back and between shoulder blades due to heavy lifting, rapid healing of swollen, blistered and sprained finger and wrist, and rapid healing of a second-degree burn;

Enhanced immune function as evidenced by a clearing up of a chronic skin infection 13 months after MePA supplementation began, a decline in frequency of upper respiratory infections, and cessation of asthma-like symptoms that had been increasing for several years prior to MePA supplementation;

More youthful skin as evidenced by less skin dryness and rash in response to hot water exposure, diminished eczema, replacement of thickened and/or numb areas on the skin with skin of normal thickness and sensation, decline in cracked skin, and recession of spider veins on feet and ankles;

Improved circulation as evidenced by decreased sensitivity to cold and better temperature control of extremities; and Improvement in psychological energy as evidenced by ability to maintain the resolve needed to successfully lose excess weight.

Participant B was a 61-year-old female in good health who experienced chronic sleep trouble. Participant B received a daily supplement of MePA according to the following dose history: (a) 1 microgram/day beginning 2016 Nov. 7; (b) 2 micrograms/day beginning 2017 Jun. 9; (c) 4 micrograms/day beginning 2017 Aug. 3; (d) 50 micrograms/day beginning 2017 Aug. 12; (e) 0 micrograms/day beginning 2017 Aug. 25; (f) 6 micrograms/day beginning 2017 Aug. 26; (g) 4 micrograms/day beginning 2017 Dec. 30; (h) 8 micrograms/day beginning 2018 Feb. 3; and (i) 6 micrograms/day beginning 2018 Mar. 12 Participant B experienced no adverse side effects from MePA supplementation.

With MePA supplementation at 1 microgram/day, Participant B reported positive health effects at three weeks. Participant B highlighted improved sleep as the greatest health benefit. Prior to treatment, the participant had slept poorly most nights and had gotten up most mornings feeling fatigued and unable to cope with the day ahead. Sleep improved after three weeks of MePA supplementation. Participant B reported feeling refreshed and rested and able to handle the normal stress and workload of life. Additional health benefits associated with MePA supplementation reported by Participant B included reduced pain, improved mental health, more youthful skin, and diminished arthritis. The following specific health benefits were reported by Participant B:

Reduced pain as evidenced by relief from chronic hip pain, chronic neck pain, and arthritic pain in finger joints;

Improved mental health as evidenced by more positive attitude, ability to cope, and a "can do" feeling;

More youthful skin as evidenced by fading of aging spots on her face; and

Diminished arthritis as evidenced by cessation of episodes of arthritic inflammation in finger joints, with lessened distortion of the fingers.

Participant C was a 70-year-old male in good health, diagnosed with biochemical recurrence of prostate cancer three years following radical prostatectomy. Participant C received a daily supplement of MePA as follows: (a) 2 micrograms/day beginning 2017 Jul. 17; (b) 4 micrograms/day beginning 2017 Jul. 23; and (c) 8 micrograms/day beginning 2018 Jan. 7. Participant C experienced no adverse side effects from MePA supplementation. Progression of Participant C's prostate cancer was monitored by medical professionals using TSA measurements. Following MePA supplementation at 2 micrograms/day for two months, progression of Participant C's prostate cancer slowed, as evidenced by both a formal statistical analysis and a simple exponential growth least squares regression model of his TSA measurements. Additional health benefits associated with MePA supplementation reported by Participant C included reduced pain and more rapid healing and more youthful skin. The following specific health benefits were reported by Participant C:

Reduced pain as evidenced by no pain from sunburn.

Rapid healing as evidenced by quick mending of a puncture wound to the palm of one hand; and More youthful skin as evidenced by cessation of chronic peeling of thickened skin on palms and soles following three months of MePA supplementation.

Participant D was an 85-year-old female who received a daily supplement of 2 micrograms/day of MePA beginning 2017 Aug. 29. Participant D experienced no adverse side effects from MePA supplementation. Prior to MePA supplementation, Participant D was visibly elderly, had difficulty standing up and getting around even with a walker, felt she had little time left to live, and had lost desire to do much of anything. These symptoms of old age began to reverse rapidly following MePA supplementation at 2 micrograms/day. Health benefits associated with MePA supplementation reported by Participant D included improved sleep, more rapid healing, improved mental health, improved heart function, increased strength, and reduced dysphagia. The following specific health benefits were reported by Participant D:

Improved sleep as evidenced by beginning to sleep soundly for the first time in years;

More rapid healing as evidenced by full restoration of her arm which had broken in a fall three years earlier, had felt weak, shrunken, and sometimes painful, but now felt normal and able to be used as previously, and as evidenced by greater resilience in two falls subsequent to beginning MePA supplementation, neither of which yielded any serious consequences and from both of which she recovered rapidly (same day);

Improved mental health as evidenced by greater initiative, renewed interest in life, rejuvenated mental acuity, feeling happier, less anxious, less depressed, more at peace and more relaxed, and also evidenced by cessation of medications for anxiety and depression, and also evidenced by restored creativity and desire to resume artistic crafts and painting;

Improved heart function as evidenced by reduced need of heart medication for atrial fibrillation;

Increased strength as evidenced by improved mobility, renewed ability to walk without walker or cane, and increased amount of walking each day;

Reduced dysphagia as evidenced by ability to eat without choking, sneezing, and difficulty swallowing.

Participant E experienced no adverse side effects from consuming a daily supplement of MePA as follows: 2 micrograms/day beginning 2017 Sep. 4 and 4 micrograms/day beginning 2017 Oct. 4. Participant E was a 59-year-old female experiencing heart failure. In April of 2016, following a long history of heart trouble, Participant E experienced two life-threatening ventricular fibrillation events within 24 hours. These were very damaging to her heart. An echocardiogram revealed that her heart was enlarging, following a path toward total heart failure. Recovery or improvement seemed impossible. The heart specialist was waiting to see how long the damaged heart could hold up before it declined enough to warrant a transplant. Against expectations, at her regular annual evaluation, two months following initiation of daily supplementation with MePA, Participant E's heart was found to no longer be declining and its enlargement was found to be somewhat decreased. Additional health benefits besides improved heart function associated with MePA supplementation reported by Participant E included improved sleep, reduced pain, more rapid healing, enhanced immune function, improved mental health, and more youthful skin. The following specific health benefits were reported by Participant E:

Improved sleep as evidenced by feeling more rested and by a reduction from 10+ hours of sleep needed per night before beginning MePA supplementation to eight hours or less a few months after beginning MePA supplementation;

Reduced pain as evidenced by relief of chronic front and back pancreatic pain;

More rapid healing as evidenced by "fantastic" (doctor's word) healing upon removal of stiches from a minor surgery incision on her hand (particularly significant since with diabetes and poor heart function, healing had been notoriously difficult);

Enhanced immune function as evidenced by a chronic yeast infection around her waist resolving;

Improved mental health as evidenced by greater wakefulness, clarity of mind, increased mental acuity, and more positive outlook;

More youthful skin as evidenced by lightening of age spots on the upper side of her forearms; and Increased energy as evidenced by cessation of overwhelming fatigue, and ability to do yard work and tend flower beds for the first time in fifteen years.

Participant F was a 63-year-old male in fair health who received a daily supplement of 2 micrograms/day of MePA beginning 2017 Sep. 11. Participant F experienced no adverse side effects from MePA supplementation. Health benefits associated with MePA supplementation reported by Participant F following five months of MePA supplementation included reduced pain, diminished headaches, more rapid healing, more youthful skin, increased energy, and improved heart function. The following specific health benefits were reported by Participant F:

Reduced pain as evidenced by a reduction in frequency of "pinched nerve" back pains and reduction in frequency and severity of hemorrhoid pain;

Diminished headaches as evidenced by a reduction in frequency of recurring "pinched nerve" headaches;

More rapid healing as evidenced by healing more quickly than expected from cuts and bruises;

More youthful skin as evidenced by healing of what Participant F believed to be a spot of (undiagnosed) skin cancer on his left cheek which had first appeared well over a year previously;

Increased energy as evidenced by eagerness to undertake strenuous wilderness hikes; and Improved heart function as evidenced by cessation of recurrent palpitations (fast beating).

Participant G was a 59-year-old female in good health, who received a daily supplement of 2 micrograms of MePA beginning 2017 Sep. 11. Participant G experienced no adverse side effects from MePA supplementation. Health benefits associated with MePA supplementation reported by Participant G following five months of MePA supplementation included reduced pain and more rapid healing. The following specific health benefits were reported by Participant G:

Reduced pain as evidenced by cessation of left heel pain which had persisted for some months; and More rapid healing as evidenced by a knee problem quickly resolving itself, which prior to MePA supplementation had caused a loss of work.

Participant H was the oldest pilot study participant. Participant H received a daily supplement of 2 micrograms of MePA beginning 2017 Sep. 28 and experienced no adverse side effects from MePA supplementation. Participant H, was an 88-year-old male in poor health. Participant H had recently been moved from a care facility to a private residence with relatives who took over his final care, as he was doing poorly and was not expected to live much longer. Participant H lived four months, significantly longer than expected, with MePA supplementation. Specific health benefits associated with MePA supplementation reported by Participant H's family care givers included increased strength and improved mental health.

Participant I was a 59-year-old female in good health who received a daily supplement of 2 micrograms of MePA beginning 2017 Oct. 2. Participant I experienced no adverse side effects from MePA supplementation. Health benefits associated with MePA supplementation reported by Participant I following six months of MePA supplementation included improved sleep, increased energy, lessened nocturia, and improved gastrointestinal function. The following specific health benefits were reported by Participant I:

Improved sleep as evidenced by Fitbit sleep records and verbal report;

Increased energy as evidenced by not feeling worn out so frequently;

Lessened nocturia as evidenced by fewer nighttime trips to the bathroom; and

Improved gastrointestinal function as evidenced by reduced frequency of constipation.

Participant J was a 62-year-old male with Mitochondrial Myopathy (MM).

Participant J experienced no adverse side effects from MePA supplementation after consuming a daily supplement of MePA as follows: (a) 2 micrograms/day beginning 2017 Oct. 8; and (b) 0 micrograms/day beginning ca. 2018 Mar. 17. MM results from a genetic defect in mitochondrial DNA, impairing ATP synthesis. MePA supplementation is not expected to reverse genetic diseases such as MM, and no improvement in MM associated with MePA supplementation was observed during the brief five and a half month trial period. Health benefits associated with MePA supplementation reported by Participant J following five months of MePA supplementation included improved sleep, lessened nocturia, and reduced hypertension.

The above working examples involving Participants A-J provide a working model of the invention to date. These examples, taken collectively, showed aging in the process of being cured in a group of ten individuals in various stages of vitamin MePA deficiency disease (i.e. aging) and exhibiting various symptoms due to the disease, having begun treatment for the disease from as much as two years and seven months ago to as little as eight months ago, as of the time of writing. That this constitutes a valid working model of the invention is most easily seen by comparison to some traditional vitamin deficiency disease. Consider the cure of pellagra via dietary supplementation with nicotinic acid, for example.

Clinically advanced pellagra is rare in the U.S. today, but before the discovery of nicotinic acid in the latter half of the 1930s, pellagra was common in the southern states where corn was a major dietary stable. The following is a description from back at that time of the effects on pellagra patients of treatment with nicotinic acid.

A comprehensive report has been made by Spies, Bean, and Ashe, based on observations at the Cincinnati General Hospital, and the Hillman Hospital, Birmingham, Ala., on the nicotinic acid treatment of hundreds of cases of classic pellagra. It is stated that: "The administration of adequate amounts of nicotinic acid or one of its compounds is followed by the disappearance of many symptoms of the disease. Within 24 to 72 hours [1 to 3 days], the fiery redness and swelling of the tongue, gums, mouth, throat, and vagina subside, and the associated Vincent's infection disappears. Within 24 to 72 hours, nausea and vomiting cease, the increased salivation decreases, and bowel movements become normal. Abdominal distention, pain and discomfort disappear and, in most cases, the desire for food returns. The acute, fiery red erythematous [reddening of the skin, usually in patches] dermal lesions, in which the epithelium [thin tissue forming the outer layer of a body's surface] is intact, blanch within 48 hours after the administration of nicotinic acid, but where the continuity of the skin is broken and the lesions are moist, ulcerated, dry or pigmented, there seems to be no specific benefit. Perhaps the most dramatic response of the pellagrin to nicotinic acid therapy is the disappearance of the acute mental symptoms. These symptoms, varying from slight confusion to delirium and mania, disappear rapidly, often overnight. The maniacal patients become calm and the confused patients, mentally clear. After therapy they become readjusted, and often have excellent insight and memory of their actions, ideas and surroundings during the psychotic period. Apathy and lassitude give way to interest." [*Physicians' Vitamin Reference Book*, third edition (New York: E. R. Squibb & Sons, January 1940), 46-47.]

Thus, treatment provided relief of diverse symptoms with no hint of any negative side-effects. This is the signature of a working model of a cure for a water-soluble vitamin deficiency disease. This signature is displayed by the working examples involving Participants A-J discussed above.

A major difference in the analogy between pellagra and MePA deficiency disease is that pellagra develops relatively quickly on a deficient diet and resolves relatively quickly on a diet appropriately supplemented with nicotinic acid, while MePA deficiency disease develops relatively slowly on a deficient diet and resolves relatively slowly on a diet appropriately supplemented with methylphosphonic acid. Fortunately, however, some of the symptoms of MePA deficiency disease begin to resolve rapidly, and because of this, the above working examples involving Participants A-J collectively furnish an easily identified working model of treatment of the MePA deficiency disease component of aging via dietary supplementation with MePA.

Participants A-J display a relief of diverse symptoms with no hint of any negative side-effects. Analogous to the report on the nicotinic acid treatment of pellagra cases quoted above, administration of adequate amounts of methylphosphonic acid is followed by the disappearance of many symptoms of the disease. Within a few weeks to a few months, the sleep disorders characteristic of aging subside. For example, there is less trouble getting to sleep (i.e., reduced insomnia), sleep is deeper and more refreshing, and less sleep is needed. Associated fatigue is reduced or disappears. The rate of wound healing is remarkably increased, and accompanying inflammation and pain is decreased. The incidence of headaches and migraines is reduced. Within a few weeks to a few months, diseases which have taken hold because of agedness, such as heart failure, cancers, and autoimmune disease, may begin to be slowed, reversed, or cured. Numerous skin disorders disappear. For example, skin becomes more moist and supple, chronic skin infections begin to clear up within a month after the administration of methylphosphonic acid, and aging spots begin slowly to fade. Perhaps the most dramatic response of the elderly to methylphosphonic acid therapy is the disappearance of chronic mental symptoms. These symptoms, varying from brain fog to depression and anxiety, disappear rapidly, sometimes within the first week. The depressed become more happy, the anxious, more calm, and the brain fogged, mentally clear. Apathy and lassitude give way to interest and creativity.

Participants A-J reported the relief of diverse symptoms with no hint of any negative side effects, which is the signature of a working model of the cure for a water-soluble vitamin deficiency disease. Thus, working examples provided by Participants A-J comprise a contemporary working model of the invention.

Example 4—Human Use of MePiA and MePA Supplementation

A woman supplements her diet with MePiA and MePA on a daily basis as described below in Table 1. A child is conceived and born to the woman. Once the child is weaned, the child's diet is supplemented with MePiA and MePA on a daily basis as summarized in Table 1 for the rest of the child's life. The child grows to adulthood, acquiring a youthful adult body which persists without aging.

TABLE 1

Useful Human Dietary Supplement of MePiA and MePA Based on Age.

| | Drops of MePiA & MePA Solution | |
| --- | --- | --- |
| Age (years) | Male | Female |
| 0-3 | See Table 2. | See Table 2. |
| 4-8 | 4 | 4 |
| 9-13 | 5 | 5 |
| 14-18 | 7 | 5 |
| 19 and older | 8 | 6 |
| Pregnant | — | 7 |
| Breast-feeding | — | 8 |

The contents of the MePiA and MePA solution are: MePiA, MePA, water, ethyl alcohol (less than 0.02%). The MePiA and MePA solution is formulated such that a drop of the solution, i.e. about 50 microliters ($\mu$L), contains 2.5 microgram ($\mu$g) of MePiA and 2.5 microgram of MePA.

For infants who are bottle fed or whose mothers are not taking MePiA and MePA supplementation, the supplementation regimen provided in Table 2 is used.

TABLE 2

Human Dietary Supplement of MePiA and MePA for Birth to Three Years.

| | Breast-feeding Is Mom Supplementing with MePiA and MePA? | | |
| --- | --- | --- | --- |
| Age | Yes | No | Not breast-feeding |
| birth through 11 months | 0 drops | 2 drops | 2 drops |
| 1 through 3 years | 0 drops | 4 drops | 4 drops |

Adequate intake of the vitamins MePiA and MePA in the early years of childhood prevents the onset of aging. Infants and toddlers who are exclusively breast-fed and whose mother is supplementing her diet with MePiA and MePA vitamins receive adequate MePiA and MePA, and no supplementation is needed. Both MePA and MePiA are water soluble and are assumed to be present in breast milk. With nearly all nutrients, the supply in the mother's milk is matched to the needs of the infant. Therefore, any physiological need that the exclusively breast-fed infant or toddler has for MePiA and MePA vitamins are satisfied simply by nursing as long as the mother is consuming MePiA and MePA vitamins.

For babies who do not breast-feed, or whose mother does not supplement with MePiA and MePA vitamins, Table 2 provides recommended supplementation with useful estimates of daily intake.

Example 5—Formulation of MePiA from Diethyl Methylphosphonite (DEMP)

About 500 mL of distilled water was added to a 1 L round flask on a heating mantel. A 1" stir bar magnet was added as a boiling chip. In a fume hood, the entire content of a 1 g commercial bottle of Diethyl Methylphosphonite (DEMP) (SKU-Pack Size 762334-1G from MilliporeSigma [formerly Sigma-Aldrich]), was added to the distilled water in the flask. The flask was stoppered using a 24/40 glass stopper and shaken to mix its contents thoroughly. Conversion of DEMP to ethyl hydrogen methylphosphinate was allowed to proceed for 15 minutes, at which time the stopper was replaced with a Snyder column prior to heating on the mantle to allow safe reflux of vapors during heating. The mixture was brought to a slow boil on the heating mantle and then cooked for a minimum of 72 hours. The solution was then allowed to cool to room temperature. The contents of the flask were poured into a 1 L graduated cylinder and distilled water was added to yield a 1.0 g/L of MePiA solution. The resulting solution was transferred to a clean 1 L amber bottle, which was capped, labeled with the date and refrigerated at about 4° C.

To determine the amounts of DEMP used and MePiA produced in the above process, the full 1 g commercial bottle of DEMP was weighed prior to use (i.e., when it was full) and when it was empty of DEMP (i.e., bottle only). As the weights of the full and empty bottle were 30.0365 g and 29.0005 g, respectively, it was determined that 1.0360 g of DEMP was employed in the above procedure, which corresponded to a theoretical yield of 0.609 g of MePiA (i.e., yield of MePiA=0.588*mass of DEMP in flask).

Example 6—Preparation of 40 mg/L of MePiA Stock Solution

About 160 mL of a 1 g/L MePiA concentrate was measured into a 1 L graduated cylinder. Distilled water was added to the graduated cylinder to bring the volume of the MePiA solution to 1 L. The resulting 1 L solution was dispensed into a clean 4 L amber jug to which 3 additional 1 L portions of distilled water were added. The jug was capped and shaken to mix. The resulting 40 mg/L of MePiA aqueous solution was dated and labeled as a stock solution for subsequent use. The stock solution was stored with a Dispensette bottletop dispenser in place of a cap and refrigerated at about 4° C.

Example 7—Preparation of MePiA Dietary Supplement

MePiA dietary supplement was formulated as a mix of equal amounts of each of MePA and MePiA from a stock solution of 40 mg/L of MePA and a stock solution of 40 mg/L of MePiA. The supplement was formulated to have a final composition of 20 mg/L of MePA and 20 mg/L of MePiA to allow delivery of about 1 μg of MePA and 1 μg of MePiA per drop or about 50 μL of supplement.

Example 8—Mice Life Span Experiment

A life span experiment was conducted with laboratory mice comparing MePA and MePiA at high daily intakes. At 24.7 weeks of age (0.48 years of age), a batch of 72, same age, female, ICR mice was randomly divided into two groups of 36 mice each and treated as follows. One group was treated with 0.1 g MePA per liter in their drinking water and the other group was treated with 0.1 g MePiA per liter in their drinking water.

Figure 2:
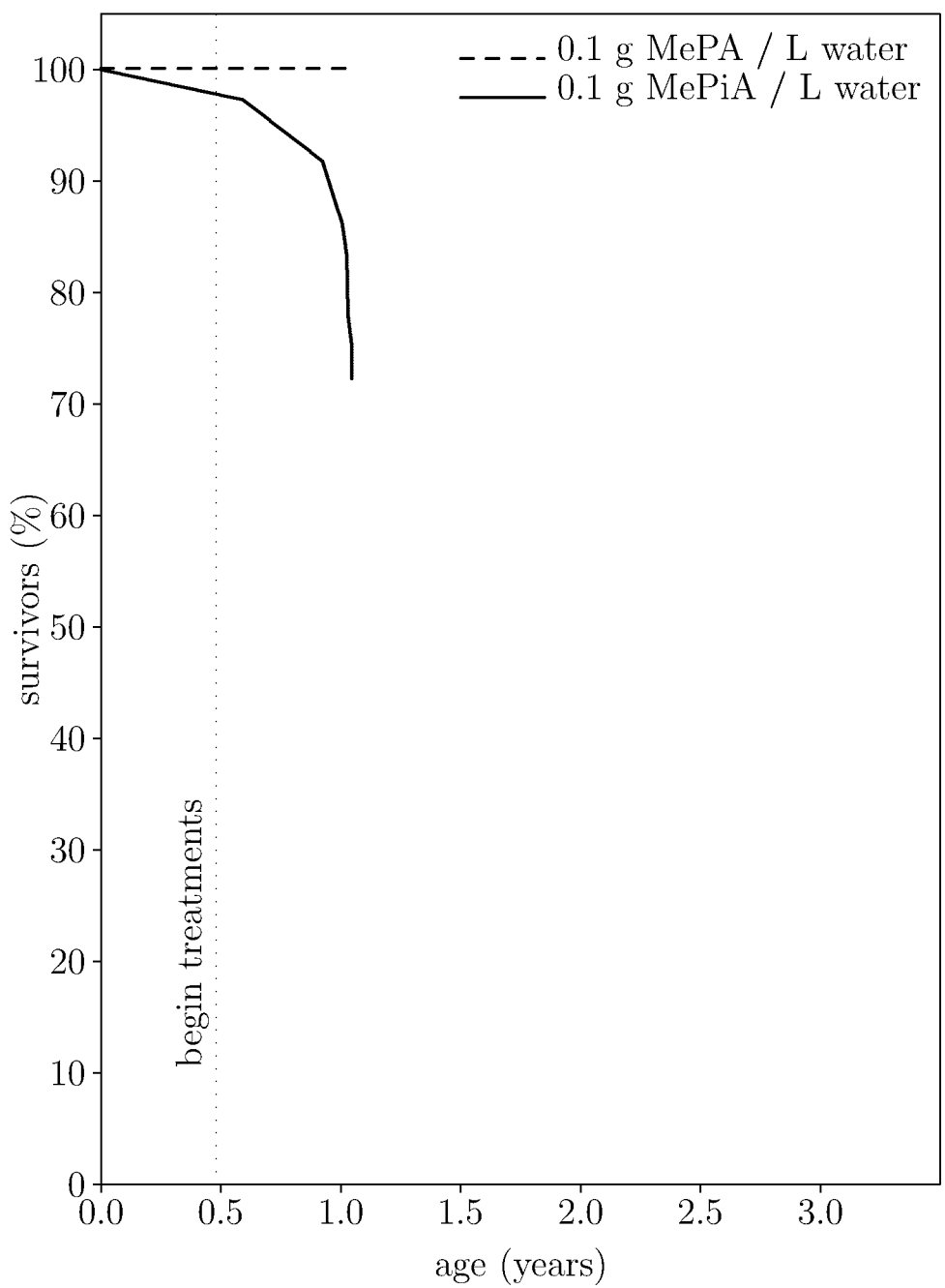
FIG. 2 are the survivorship curves of 72 ICR (Harlan) female mice that were just over a year old and six months into treatment with 0.1 g/L (0.01% weight/volume) of MePA (36 mice) or 0.1 g/L (0.01% weight/volume) of MePiA (remaining 36 mice).

Early results shown in FIG. 2 were obtained when the mice were just over a year old and had been treated with MePA/MePiA for about six months. None of the MePA-treated mice had died up to that point. In sharp contrast, more than a quarter of the MePiA-treated mice had died. Relative to previous batches of similar mice raised over the course of nearly two decades in the ARP rodent lab, the MePA mice were doing unusually well and the MePiA mice were doing unusually poorly, a surprising result as water-soluble vitamins are notoriously very low in toxicity.

Treatments were maintained for another year despite this negative result with MePiA. At 110 weeks (2.1 years) of age, roughly half of all of the mice had died. While the juvenile die-off of MePiA mice had ameliorated, MePA survival had consistently outperformed MePiA survival. The treatment regimen the mice had been on for over a year and a half was then suspended.

Eventually, at 161 weeks (3.1 years) of age, when only three of the original 72 mice were still alive, two of the surviving mice looked to be very aged mice, but the third mouse looked younger than expected. The batch of 72 mice used in this experiment were the last batch of mice to enter the lab. They had entered the lab as weanlings. They were the youngest mice in the lab, and they were all of the same age. There had at no point been any younger mice available to accidentally put in the wrong cage. It appeared that this one mouse was, in fact, physiologically younger than her chronological age—that she had experienced life-lengthening.

The two elderly-looking mice died at 159 weeks (3.04 years) and 160 weeks (3.06 years) of age. The younger-looking mouse remained alive until 172 weeks (3.29 years) of age. She was the last mouse in the rodent lab at that time, and she is the oldest mouse the lab has produced in its nearly two decades of operation.

Figure 3:
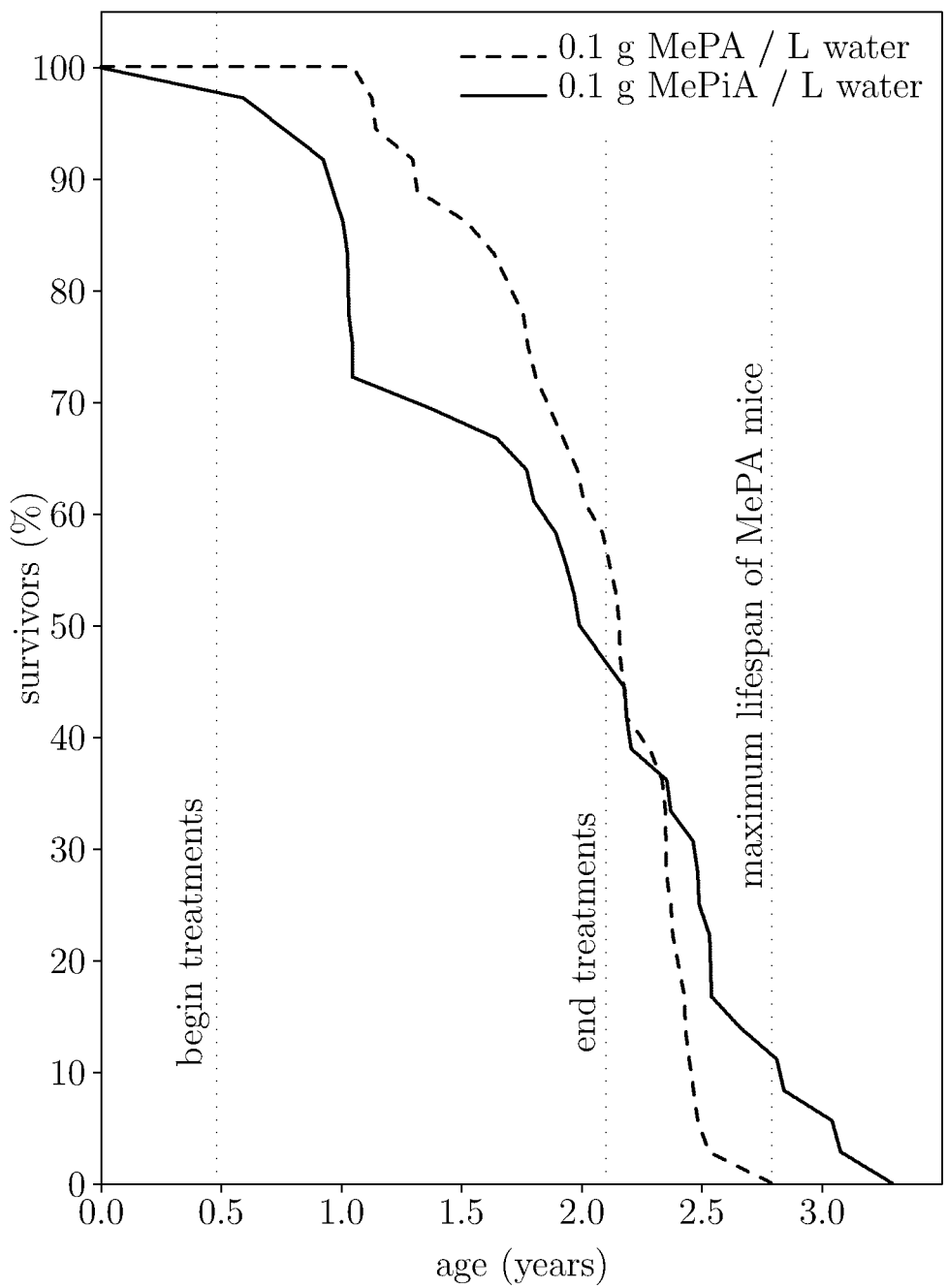
FIG. 3 are the final survivorship curves of the 72 female mice of FIG. 2.

FIG. 3 provides the final survival curves for the 72 mice. Contrary to expectation, the percentage of survivors in the group of MePiA-treated mice surpassed the percentage of survivors in the group of MePA-treated mice. From the perspective of aging, the maximum life span for the MePiA-treated mice was greater than the maximum life span for the MePA-treated mice. These results illustrated life lengthening in the MePiA-treated mice (including the two elderly-looking mice and the younger-looking mouse) relative to the MePA-treated mice and are evidence of increased maximum life span.

Figure 4:
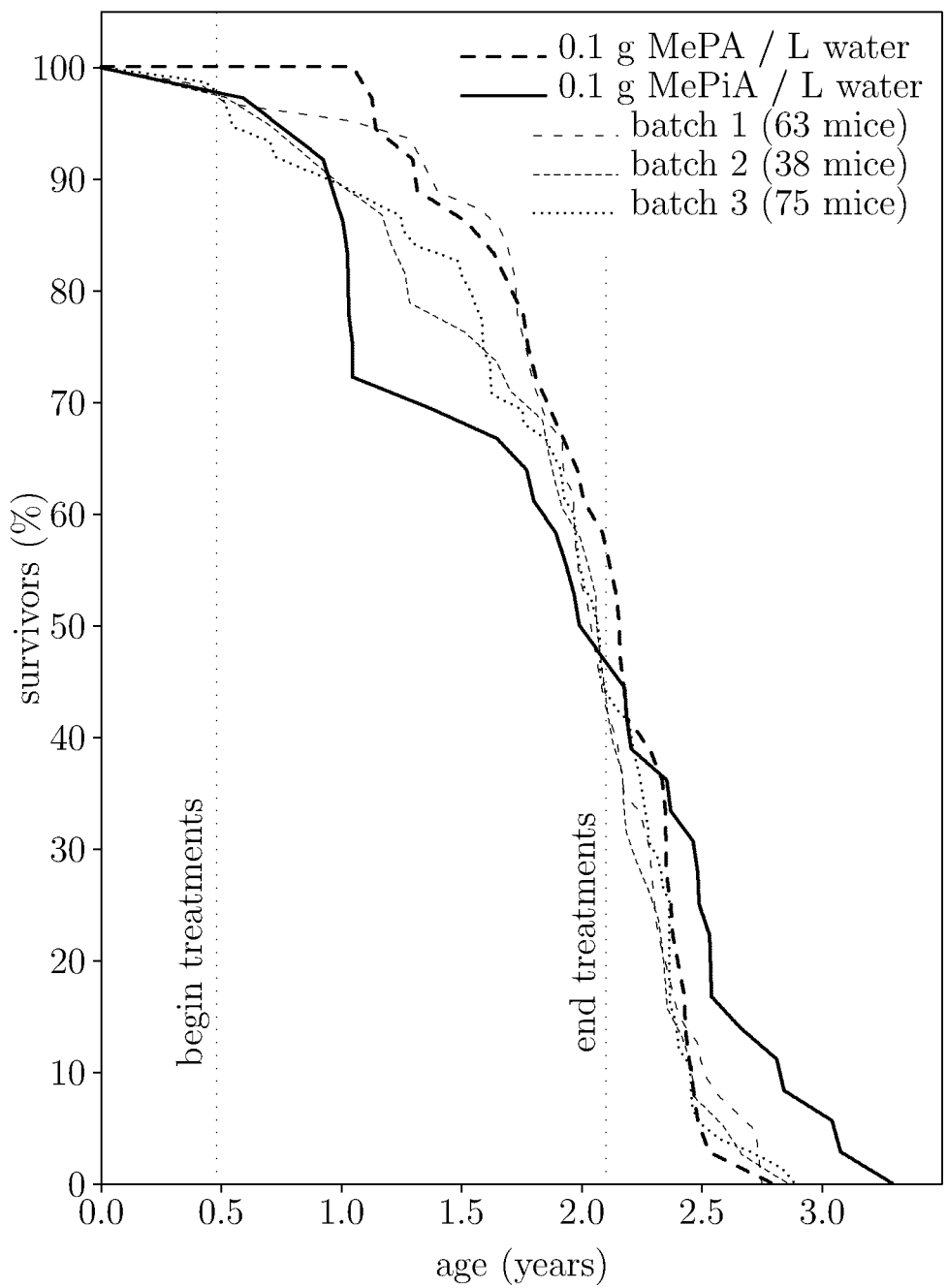
FIG. 4 are the survivorship curves of same age, ICR (Harlan) female weanling mice subjected to a variety of treatments intended to induce life lengthening including treatment with MePiA/MePA (batch 4).

FIG. 4 provides survival curves for batches of same age, weanling, female, ICR mice subjected to a variety of treatments intended to induce life lengthening. The MePiA/MePA-treated mice were batch 4. As shown in FIG. 4, the survival curve for the MePA-treated mice of batch 4 was similar to the other three batches while the survival curve of the MePiA-treated mice of batch 4 was different. MePiA treatment appeared to have extended the maximum life span for these mice.

Example 9—Toxicity of MePiA

Analysis of the early data discussed above indicated that the juvenile die-off seen in the MePiA-treated mice data was almost exclusively within a single cage of mice. The mice were housed in large cages, nine mice per cage. By the end of the juvenile die-off, only three mice remained in this one cage. The other three MePiA-treated cages had six, eight, and nine survivors at this stage. This was an improbable distribution of deaths if the juvenile die-off was assumed to be due to toxicity. To determine whether the die-off was a treatment-unrelated random event, such as the presence of an infectious agent in the depleted cage, rather than toxicity, a subsequent, brief (14 weeks) treatment of another batch of mice (33 treated and 33 untreated) was performed. In this subsequent treatment, mice were administered ten times the dose previously administered (i.e., 1 g/L of MePiA). Results obtained indicated no signs of toxicity. At the end of the 14 weeks, only one treated mouse and two untreated mice had died.

Figure 5:
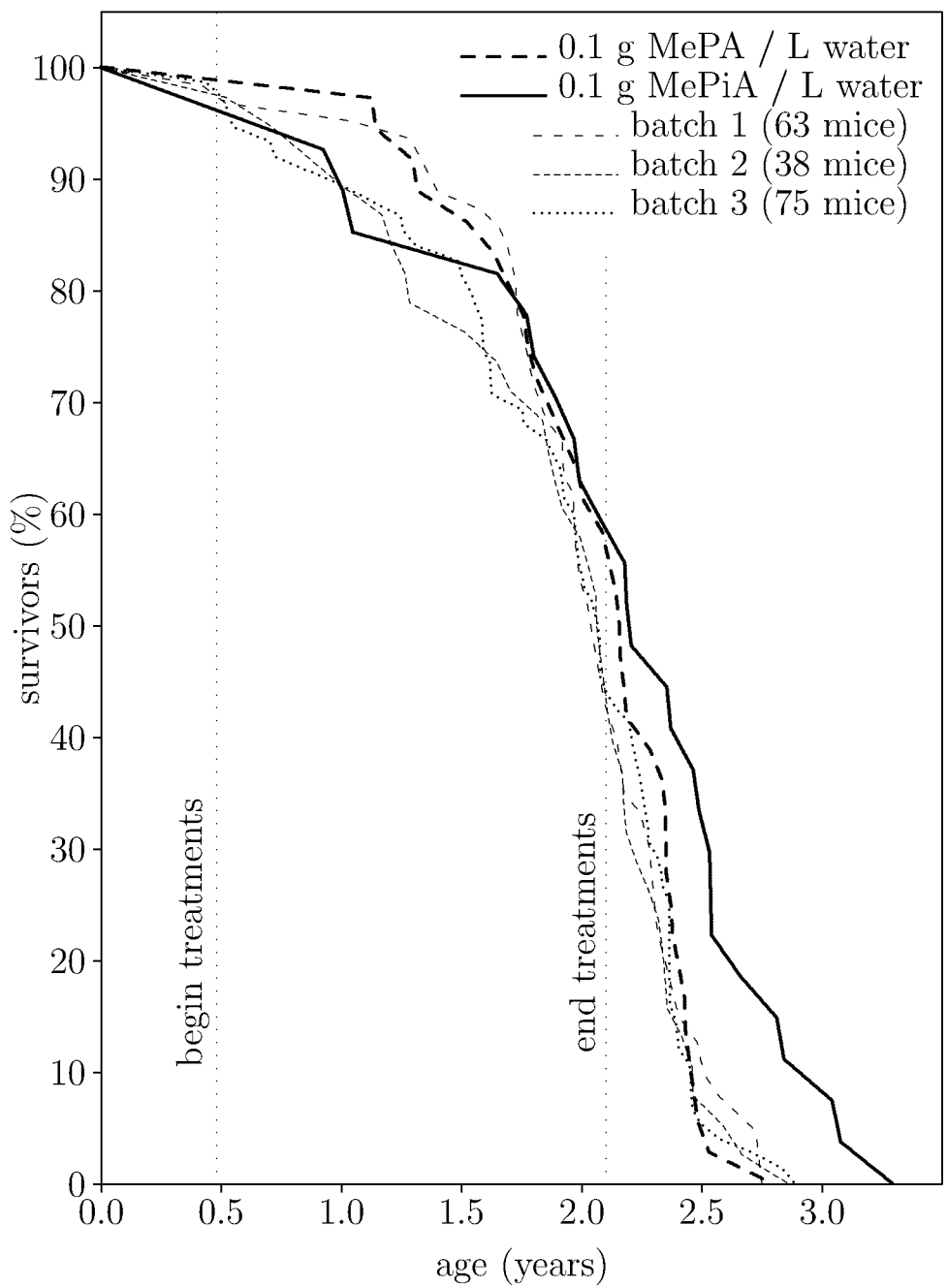
FIG. 5 are the survivorship curves of the ICR (Harlan) female weanling mice data set presented in FIG. 4 in which data from the depleted, infected cage have been excluded.

FIG. 5 represents results obtained when all mice from the depleted and suspected infected cage were excluded from the dataset. Consistent with FIG. 4, FIG. 5 showed an extension of maximum life span for mice treated with MePiA.

A similar observation was seen with the three longest surviving mice. The two elderly-looking mice were raised together in the same cage, separate from the younger-looking mouse. Thus, they were likely dying of a common disease that gave them a particularly haggard appearance unrelated to physiological agedness.

Example 10—Conclusions

The evidence that a minimum of 50% of the MePiA mice lived longer than they would have without MePiA (e.g., FIG. 5) indicated that supplementation with MePiA lengthened life spans of the mice.

For the first six months of their lives, before treatment with MePA/MePiA began, batch 4 mice aged at a normal rate due to mitochondrial degradation occasioned by free radicals generated within their mitochondria. Following initiation of treatments, MePA-treated mice continued to age at a normal rate, MePA being resistant to oxidation and hence offering no protection against free radicals. Meanwhile, aging in MePiA-treated mice was slowed due to the presence in their mitochondria of easily oxidized MePiA.

When treatment ceased, a normal rate of aging resumed in the MePiA-treated mice. But the mitochondria of these MePiA-treated mice had suffered less damage than the mitochondria of MePA-treated mice throughout the treatment phase. As a result, the mitochondria of MePiA-treated mice were able to sustain post-treatment damage for a longer time than the mitochondria of MePA-treated mice before critical damage levels, resulting in death, were reached. This evidences as lengthened life spans of the MePiA-treated mice relative to the MePA-treated mice.

Some MePiA-treated mice (possibly the younger-looking mouse) may possess genetics necessary to actively support the natural antioxidant role played by MePiA in the mitochondria, maximizing MePiA's effectiveness against free radicals in that location. This includes the possibility of transport proteins able to actively transport MePiA molecules into the mitochondria, concentrating and keeping them there, as well as enzymes to recycle/reactivate MePiA molecules following their reaction with free radicals in the mitochondria. Thus, in this case, cessation of treatment does not result in immediate loss of mitochondrial protection. For these MePiA-treated mice, MePiA sequestered and recycled in the mitochondria may go on providing protection for a long time.

This MePiA mitochondrial free radical theory of aging provides an explanation not only of the FIG. 5 data, but also of historic human life span data implying existence of an anti-aging vitamin. A mathematical model of that data found a lifetime for the anti-aging vitamin in the human body of 194±4 years, giving a biological half-life of 135±3 years. This is a remarkably long biological half-life, which seems to imply specialized mechanisms for conservation of the anti-aging vitamin similar to those discussed for MePiA-treated mice in the previous paragraph.

While vitamin MePA was found to bestow numerous health benefits on humans, the mice data of FIG. 5 show that maximum life span increased when the diet was supplemented with vitamin MePiA. Because MePiA can be oxidized to MePA, dietary supplementation with MePiA can make MePA available by in vivo oxidation of MePiA to MePA. The body's need for MePA may be met in this way, however, both MePiA and MePA can be supplemented together in the diet. Inclusion of both MePA and MePiA in animal (including human) diets can prevent or cure aging and extend maximum life spans.

What is claimed is:

1. A composition comprising methylphosphinic acid or a salt thereof and a pharmaceutically acceptable ingredient.

2. The composition of claim 1, which is a liquid, wherein the methylphosphinic acid or a salt thereof is at a concentration of about 2 mg/L to about 600 mg/L.

3. The composition of claim 2, which is a beverage, wherein the methylphosphinic acid or a salt thereof is at a concentration of about 0.005 mg/L to about 1 mg/L.

4. The composition of claim 3, further comprising methylphosphonic acid or a salt thereof.

5. The composition of claim 4, which comprises about equal amounts of (a) the methylphosphinic acid or a salt thereof, and (b) the methylphosphonic acid or a salt thereof.

6. The composition of claim 1, which is a solid that comprises about 0.3 mg to about 2 g of the methylphosphinic acid or a salt thereof per kilogram of the solid.

7. The composition of claim 1, which is prepackage food that comprises about 0.01 mg to about 5 mg of the methylphosphinic acid or a salt thereof per kilogram of the prepackaged food.

8. The composition of claim 7, further comprising methylphosphonic acid or a salt thereof.

9. The composition of claim 8, which comprises about equal amounts of (a) the methylphosphinic acid or a salt thereof, and (b) the methylphosphonic acid or a salt thereof.

10. The composition of claim 6, which is a powder that comprises about 1 mg/kg to about 2 g/kg of the methylphosphinic acid or a salt thereof.

11. A method for reducing aging in a mammal in need thereof, the method comprising administering the composition of claim 1 to the mammal.

12. A composition consisting essentially of methylphosphinic acid or a salt thereof and one or more pharmaceutically acceptable ingredients.

13. The composition of claim 12, which further includes methylphosphonic acid or a salt thereof.

14. The composition of claim 12, which is a liquid consisting essentially of about 0.005 mg/L to about 600 mg/L of the methylphosphinic acid or a salt thereof.

15. The composition of claim 12, which is a solid consisting essentially of about 0.01 mg/kg to about 2 g/kg of the methylphosphinic acid or a salt thereof.

16. A method for reducing aging in a mammal in need thereof, the method comprising administering the composition of claim 12 to the mammal.

* * * * *